US011073492B2

(12) United States Patent
Ushigome et al.

(10) Patent No.: US 11,073,492 B2
(45) Date of Patent: Jul. 27, 2021

(54) SENSOR DEVICE, METHOD FOR PRODUCING SAME, AND GAS SENSOR

(71) Applicant: FUJITSU LIMITED, Kawasaki (JP)

(72) Inventors: Michio Ushigome, Atsugi (JP); Osamu Tsuboi, Kawasaki (JP); Kazuaki Karasawa, Hadano (JP)

(73) Assignee: FUJITSU LIMITED, Kawasaki (JP)

( * ) Notice: Subject to any disclaimer, the term of this patent is extended or adjusted under 35 U.S.C. 154(b) by 496 days.

(21) Appl. No.: 16/170,101

(22) Filed: Oct. 25, 2018

(65) Prior Publication Data

US 2019/0137428 A1 May 9, 2019

(30) Foreign Application Priority Data

Nov. 8, 2017 (JP) .............................. JP2017-215652

(51) Int. Cl.
*G01N 27/12* (2006.01)
*G01N 33/497* (2006.01)
*A61B 5/08* (2006.01)

(52) U.S. Cl.
CPC ........... *G01N 27/126* (2013.01); *A61B 5/082* (2013.01); *G01N 33/497* (2013.01); *A61B 2562/125* (2013.01); *G01N 27/129* (2013.01)

(58) Field of Classification Search
CPC .... G01N 27/12; G01N 27/126; G01N 33/497; A61B 5/082
See application file for complete search history.

(56) References Cited

U.S. PATENT DOCUMENTS

| | | | | |
|---|---|---|---|---|
| 6,985,082 B1* | 1/2006 | Dutta | ..................... | G01N 27/12 340/632 |
| 2011/0124113 A1* | 5/2011 | Azad | .................. | G01N 33/5438 436/139 |
| 2012/0186987 A1* | 7/2012 | Mirsky | ................ | G01N 27/126 205/334 |
| 2016/0025517 A1* | 1/2016 | Giedd | ...................... | G01K 7/16 324/691 |
| 2016/0035456 A1* | 2/2016 | Sauro | ....................... | H01B 1/24 252/511 |
| 2016/0341717 A1* | 11/2016 | Momose | ................ | G01N 27/12 |
| 2017/0067847 A1* | 3/2017 | Momose | ............ | G01N 27/4071 |
| 2017/0067850 A1* | 3/2017 | Momose | ................. | H01L 29/47 |
| 2017/0254767 A1* | 9/2017 | Karasawa | .......... | G01N 33/0009 |
| 2017/0336345 A1* | 11/2017 | Momose | ............ | G01N 27/4141 |

(Continued)

FOREIGN PATENT DOCUMENTS

JP      H03-37559 A      2/1991
JP      2016-217756 A    12/2016

OTHER PUBLICATIONS

Pascal Lauque, et al., "Highly Sensitive and Selective Room Temperature NH3 Gas Microsensor Using an Ionic Conductor (CuBr) Film", Analytica Chimica Acta 515 (2004), pp. 279-284 (Total 6 pages).

(Continued)

*Primary Examiner* — Nathaniel J Kolb
(74) *Attorney, Agent, or Firm* — Fujitsu Patent Center

(57) ABSTRACT

A sensor device includes a first electrode and a second electrode disposed over a substrate, and a sensitive film including a base film which couples the first electrode and the second electrode to each other and contains Cu and a halogen element and PEDOT/PSS which bonds to the base film.

20 Claims, 15 Drawing Sheets

(56) References Cited

U.S. PATENT DOCUMENTS

2017/0350839 A1* 12/2017 Momose ................ G01N 27/12
2018/0024083 A1*  1/2018 Yoshioka ............. G01N 27/126
                                                    324/693
2018/0038822 A1*  2/2018 Momose ............ G01N 27/4075

OTHER PUBLICATIONS

Rita Stella, et al., "Characterisation of Olive Oil by an Electronic Nose Based on Conducting Polymer Sensors", Sensors and Actuators B 63 (2000), pp. 1-9 (Total 9 pages).

* cited by examiner

SENSOR DEVICE, METHOD FOR PRODUCING SAME, AND GAS SENSOR

CROSS-REFERENCE TO RELATED APPLICATION

This application is based upon and claims the benefit of priority of the prior Japanese Patent Application No. 2017-215652, filed on Nov. 8, 2017, the entire contents of which are incorporated herein by reference.

FIELD

The embodiments discussed herein are related to a sensor device, a method for producing the sensor device, a gas sensor, and information processing system.

BACKGROUND

In advanced nations increasingly heading for an aging society, when aging further proceeds, a large number of people will be nursed or cared for by a small number of people. Thus, an era in which full medical service is not provided will come. Under such circumstances, individuals have come to be expected on a higher level to prevent life-style related diseases, and there has been a demand for a more convenient noninvasive examination method.

The related art is disclosed in Japanese Laid-open Patent Publication No. 2016-217756, Japanese Laid-open Patent Publication No. 3-37559, Non Patent Literature 1: P. Lauque et al., "Highly sensitive and selective room temperature NH3 gas microsensor using an ionic conductor (CuBr) film", Analytica Chimica Acta 515 (2004) 279-284, and Non Patent Literature 2: R. Stella et al., "Characterisation of olive oil by an electronic nose based on conducting polymer sensors", Sensors and Actuators B 63 (2000) 1-9.

SUMMARY

According to an aspect of the embodiments, a sensor device comprising: a first electrode and a second electrode disposed over a substrate; and a sensitive film including: a base film which couples the first electrode and the second electrode to each other and contains Cu and a halogen element; and PEDOT/PSS which bonds to the base film.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

For example, metabolites generated in the human body are exhaled as breath. Thus, the species and concentrations of gases contained in human breath are considered as being significantly influenced by the functioning state of internal organs. For example, in breath gas sensing, a specific component in human breath is sensed and monitored, to thereby noninvasively determine the state of human health or initial symptoms of a disease.

Aldehydes are used as breath biomarkers. For example, nonanal may be used as a biomarker for lung cancer, and acetaldehyde may be used as a biomarker for cancer of the esophagus. For example, in the mortality by cancer site, the mortality of lung cancer has rapidly increased in these years and has reached the highest mortality; this trend of an increase in the mortality seems to continue. Thus, determination based on nonanal is very effective.

For example, an ammonia sensor for detecting ammonia may be proposed.

Human breath contains aldehyde in a very low concentration. For this reason, in order to sense the aldehyde, a sensor device having very high sensitivity is prepared. Breath gas simultaneously contains a large number of gas species, for example. Thus, in order to selectively detect aldehyde from these gases, the sensor desirably has high sensitivity to other gas species. However, for detecting an aldehyde such as nonanal, sensor devices have very high resistance for gas sensors, and have not been implemented for gas sensors.

For example, the problem of a sensor device used for a breath gas sensor among gas sensors similarly exists in a sensor device used for another gas sensor such as an odor sensor. For example, the problem of a sensor device for detecting aldehyde similarly exists in a sensor device for detecting ketone, for example.

For example, a sensor device for detecting aldehyde or ketone with high sensitivity, and a gas sensor including the sensor device may be provided.

For example, the sensor device may be a gas sensor device used for a gas sensor. For example, the sensor device is used for a gas sensor such as a breath gas sensor for detecting a specific component in human breath, or an odor sensor for detecting, for example, an odor of food or old person smell, and is configured to detect, in rapid response with high sensitivity, particularly, for example, aldehyde contained in gases such as breath gas or odors such as those of foods or old person smell.

Figure 2:
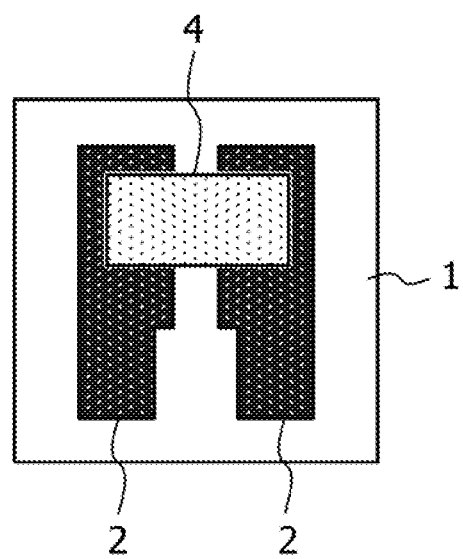
FIG. 2 is an example of a plan view of a sensor device.

Thus, the gas sensor may also be referred to as an aldehyde sensor. The sensor device may also be referred to as an aldehyde sensor device. As Illustrated as FIG. 2, a sensor device according to this embodiment includes a first electrode 2 and a second electrode 3 disposed on a substrate 1, and a sensitive film 4 connecting the first electrode 2 and the second electrode 3 to each other. The sensitive film 4 is a film for adsorbing a detection target gas, and is disposed so as to extend over a pair of electrodes that are the first electrode 2 and the second electrode 3.

Figure 1:
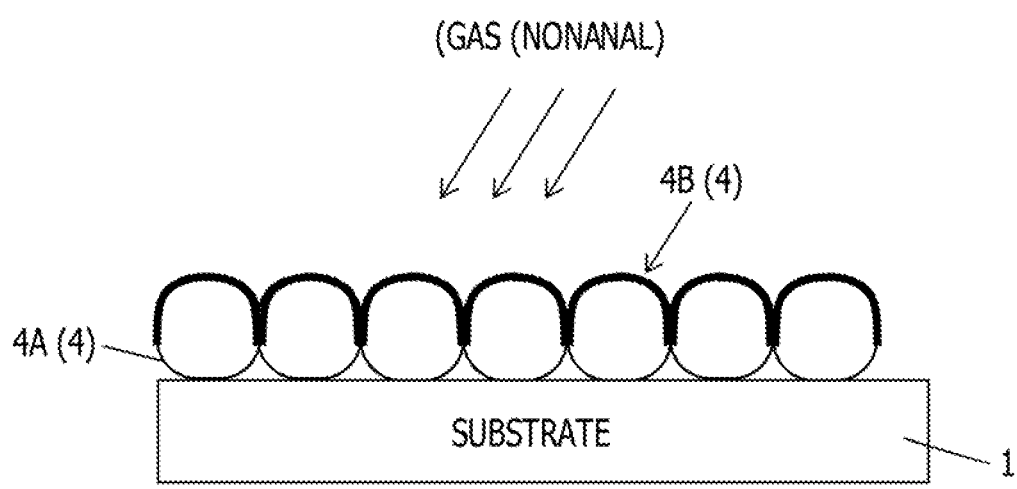
FIG. 1 is an example of a sectional view of a sensitive film of a sensor device.

As illustrated as FIG. 1, the sensitive film 4 includes a base film 4A containing Cu (copper) and a halogen element, and poly(3,4-ethylenedioxythiophene)/poly(styrene sulfonate) (PEDOT/PSS) 4B bonding to the base film 4A. In the embodiment, the base film 4A is a copper halide film, specifically, a cuprous bromide (CuBr) film, for example.

Thus, the PEDOT/PSS 4B is used for a portion (of the sensitive film 4) for adsorbing a detection target gas, and the CuBr film 4A responding rapidly with high sensitivity is used as the base film (base material); and, the PEDOT/PSS 4B and the CuBr film 4A bonded together constitute the sensitive film 4. This provides a gas sensor device for detecting aldehyde in rapid response with high sensitivity, and a gas sensor including the gas sensor device.

PSS and PEDOT each have low electroconductivity, whereas the PEDOT/PSS 4B has sufficiently high electroconductivity.

The PEDOT/PSS 4B is obtained as an aqueous dispersion of fine particles by oxidative polymerization of 3,4-ethylenedioxythiophene (EDOT) in the presence of PSS in water. PEDOT itself is a π conjugated polymer, while PSS plays the role of a dopant and aqueous dispersant. However, the PEDOT/PSS 4B has a very high resistance value for a gas sensor, and hence it is difficult to use the PEDOT/PSS 4B for the sensitive film 4 to provide a gas sensor device.

On the other hand, the CuBr film 4A has high electroconductivity, is used for, for example, a sensitive film of a sensor device of an ammonia sensor, and has excellent features of responding rapidly with high sensitivity. The PEDOT/PSS 4B is used for a portion (of the sensitive film 4) for adsorbing a detection target gas, and the CuBr film 4A is used for the base film; and, the PEDOT/PSS 4B and the CuBr film 4A bonded together to constitute the sensitive film 4. This enables a decrease in the resistance to a resistance for a gas sensor, and provides a gas sensor device for detecting aldehyde in rapid response with high sensitivity, and a gas sensor including the gas sensor device.

When the sensitive film 4 has a high resistance, measurement is performed not with a simple measurement circuit, but with a large measurement apparatus, which is impractical. By contrast, the sensitive film 4 is constituted as described above to have a lower resistance, which enables measurement by a relatively simple method to thereby enable a gas sensor. In this embodiment, as illustrated as FIG. 1, the PEDOT/PSS 4B bonds to the grain boundaries of crystal grains constituting the CuBr film 4A serving as the base film, and the surfaces of the crystal grains.

For example, the sensitive film 4 is a film in which the PEDOT/PSS 4B is bonded to (adsorbed onto) the grain boundaries of crystal grains constituting the CuBr film 4A serving as the base film, and the surfaces of the crystal grains. The sensitive film 4 includes the CuBr film 4A in which a plurality of crystal grains (for example, a plurality of crystal grains having different sizes) are two-dimensionally arranged; PSS bonding to the CuBr film 4A along the plurality of crystal grains constituting the CuBr film 4A; and PEDOT adsorbed onto the PSS.

Figure 3:
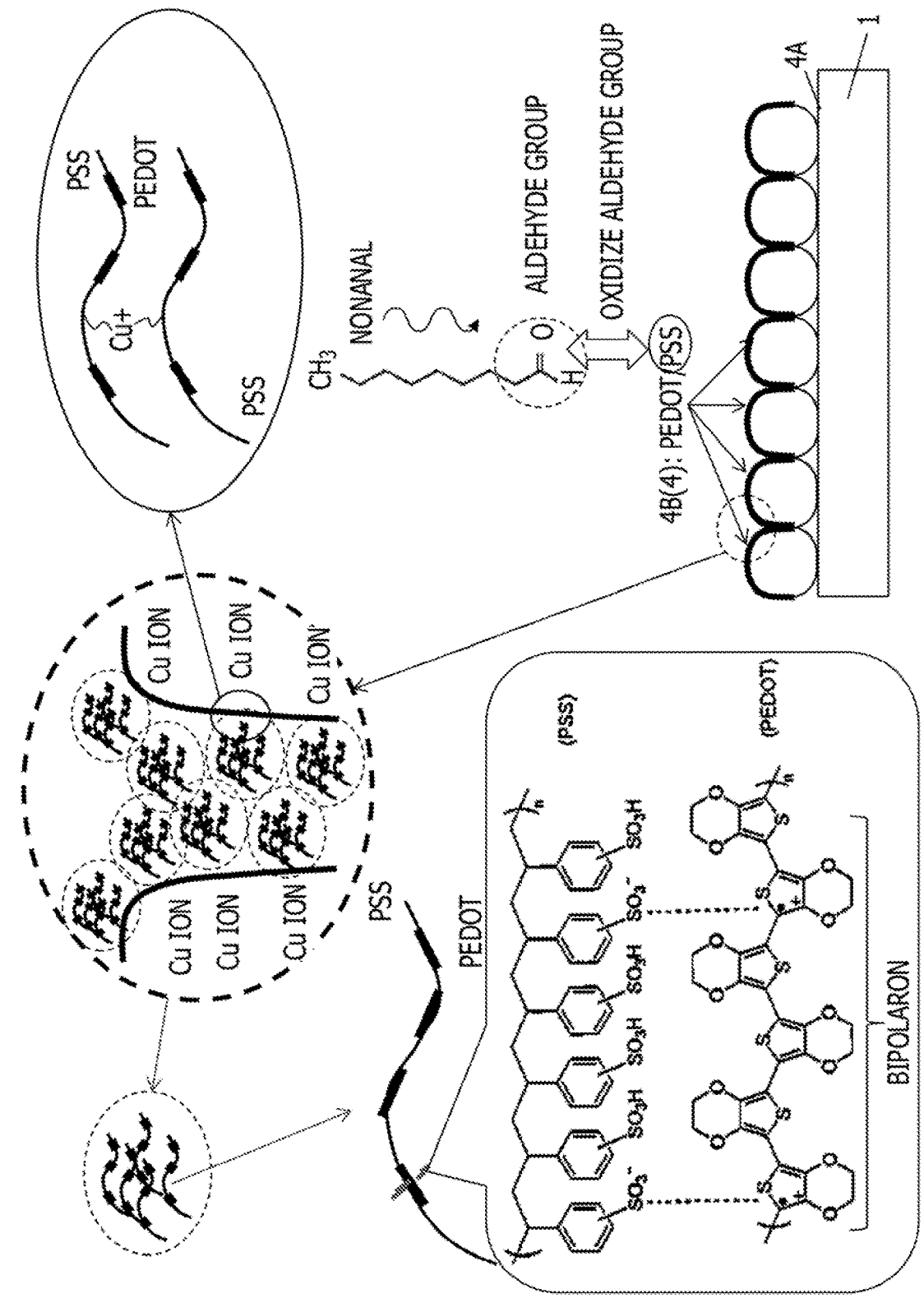
FIG. 3 illustrates an example of the configuration of a sensitive film of a sensor device and adsorption of nonanal onto the sensitive film.

In this case, PEDOT/PSS chains 4B have a characteristic of being cross-linked via $Cu^+$, so that PEDOT/PSS covering the surfaces of crystal grains constituting the CuBr film uniformly bonds so as to conform to the irregular profile, which results in an increase in the surface area for adsorbing aldehyde (for example, refer to FIG. 3). Thus, the area for adsorbing aldehyde is increased, to thereby increase a variation in the electrical resistance value for the concentration of aldehyde, which enables detection of aldehyde in rapid response with high sensitivity.

The method for producing the sensor device constituted as described above may include a step of forming the first electrode 2 and the second electrode 3 on the substrate 1; a step of forming a Cu film so as to connect the first electrode 2 and the second electrode 3 to each other; and a step of forming the sensitive film 4 by treating a Cu film 4X with a treatment liquid containing Cu and a halogen element and prepared by adding PEDOT/PSS, the sensitive film 4 including the base film 4A containing Cu and the halogen element, and the PEDOT/PSS 4B bonding to the base film 4A (for example, refer to FIGS. 5A to 5E).

The sensor device has a structure as illustrated as FIG. 1: on the surface of the substrate 1 (for example, a Si substrate having a thermal oxidation film), CuBr crystal grains having a grain size of, for example, about 500 nm to about 800 nm are densely arranged to form the CuBr film 4A; and the PEDOT/PSS 4B enters the surface and crystal grain boundaries of the CuBr film 4A.

This film structure inferentially provides the following sensing mechanism (refer to FIG. 3). PEDOT includes about 6 to about 18 EDOT units bonding together, and PEDOT has a much shorter chain than PSS. Thus, the PEDOT/PSS 4B has a structure in which a large number of short PEDOTs adhere to a long PSS, and such structures intertwine with one another and aggregate to provide a three-dimensional structure. In this case, PEDOT adheres to PSS, and PSS oxidizes PEDOT.

Only portions where PEDOT adheres to PSS have electroconductivity, and metal ions present near PEDOT/PSS (units) 4B tend to bond to the PEDOT/PSS 4B to cross-link the PEDOT/PSS 4B. Thus, Cu ions near the surface and crystal grain boundaries of the CuBr film 4A cross-link the PEDOT/PSS 4B together, to ensure contact between the CuBr film 4A and the PEDOT/PSS 4B.

Thus, the sensitive film 4 of the sensor device has a structure in which the PEDOT/PSS 4B bonds to the surfaces and crystal grain boundaries of crystal grains constituting the CuBr film 4A. As illustrated as FIG. 3 and FIG. 4, when an aldehyde gas (represented by nonanal gas in FIG. 3 and FIG. 4) comes close to the surface of the sensitive film 4 and enters the PEDOT/PSS 4B, nonanal gas molecules mainly adsorb onto PSS between PEDOT and PEDOT, namely, non-adsorption portions of PSS (portions to which PEDOT does not adhere; portions denoted by symbol X in FIG. 4), and PSS oxidizes the aldehyde group moiety of nonanal (refer to FIG. 3). This enables a decrease in the resistance of the sensor device (the resistance of the gas sensor; the resistance of the sensitive film).

Figure 4:
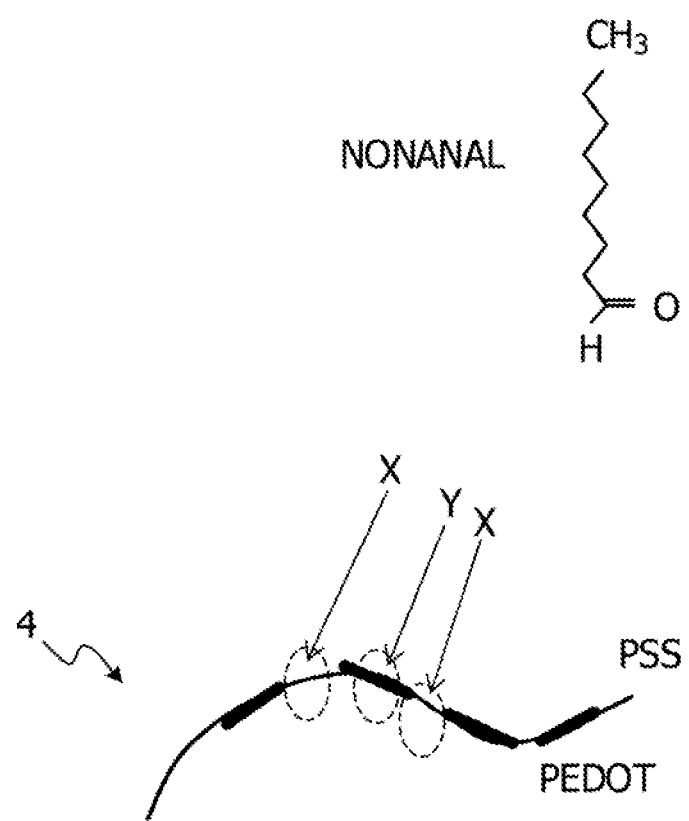
FIG. 4 illustrates an example of adsorption of nonanal onto a sensitive film of a sensor device.

When nonanal gas molecules adsorb and, as a result, non-adsorption portions (portions denoted by symbol X in FIG. 4) of PSS are no longer left, nonanal gas molecules come to adsorb onto PEDOT-adhesion portions of PSS (portions denoted by symbol Y in FIG. 4). This gradually degrades adhesion of PEDOT to PSS, which causes a decrease in the electroconductivity and an increase in the resistance of the sensor device (the resistance of the gas sensor; the resistance of the sensitive film).

Thus, when the gas sensor (sensor device) is used immediately after its completion, it responds to nonanal to cause a decrease in the resistance. However, when the gas sensor (sensor device) is sufficiently aged by, for example, being kept in a sufficient contact with nonanal gas, nonanal gas molecules adsorb onto non-adsorption portions of PSS and the non-adsorption portions of PSS are no longer left. In this case, the gas sensor (sensor device) responds to nonanal to cause an increase in the resistance. This enables a larger response and higher sensitivity as in a second modification described later.

Figure 5A:
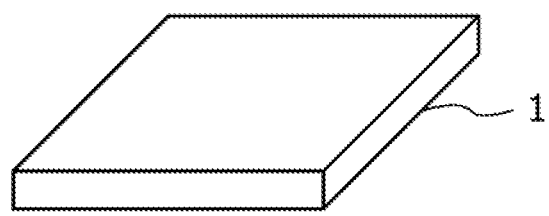
FIG. 5A to FIG. 5E illustrate an example of a method for producing a sensor device.

As illustrated as FIG. 5A, the substrate 1 (for example, a Si substrate having a thermal oxidation film) is prepared. As illustrated as FIG. 5B, gold (Au) is deposited on the surface of the substrate 1 to form two gold electrodes (Au electrodes: thickness of about 60 nm; the first electrode 2 and the second electrode 3). The two gold electrodes 2 and 3 are provided with a gap width of about 1 mm therebetween. This step is a step of forming the first electrode 2 and the second electrode 3 on the substrate 1.

Under the gold electrodes 2 and 3, Ti (film thickness: about 10 nm) and Pt (film thickness: about 50 nm) may be deposited to form an adhesion layer. The substrate 1 is a substrate that at least avoids direct electrical connection between the two electrodes 2 and 3, and is not limited to the Si substrate having a thermal oxidation film. For example, a Si substrate having a $TiO_2$ thin film deposited may be used.

For example, a resin substrate may be used as long as the electrodes 2 and 3 (here, Au) and the sensitive film 4 (here, in particular, for example, Cu for forming the CuBr film 4A serving as the base film) described later are formable by deposition.

Examples of the resin forming the substrate 1 include PE (polyethylene), PP (polypropylene), PVC (polyvinyl chloride), PS (polystyrene), PVA (polyvinyl acetate), PUR (polyurethane), PTFE (polytetrafluoroethylene), ABS resin, PMMA, PA (polyamide), POM (polyacetal), PC (polycarbonate), PET (polyethyleneterephthalate), PBT (polybutyleneterephthalate), PPS (polyphenylene sulfide), PSF, PEEK, PI (polyimide), and PAI (polyamide-imide). The substrate 1 may be a substrate provided by coating a conductor with such a resin.

The gold electrodes 2 and 3 are not particularly limited in terms of film thickness. However, when the film thickness is too small, for example, about 20 nm or less, the film may separate; thus, the film thickness is preferably about 60 nm, for example. The two electrodes 2 and 3 are formed of Au (gold); however, this is not limiting, and a material having a higher electroconductivity than the sensitive film 4 (here, the PEDOT/PSS 4B and the CuBr film 4A) is used.

For example, Ag (silver), Pt (platinum), Cu (copper), Al (aluminum), Hg (mercury), W (tungsten), Ir (iridium), Fe (iron), or C (carbon) may be used, or an electroconductive alloy containing the foregoing may be used. The material is not limited to inorganic materials, and an electroconductive polymer material having a higher electroconductivity than the sensitive film 4 (here, the PEDOT/PSS 4B and the CuBr film 4A) may be used.

Figure 5B:
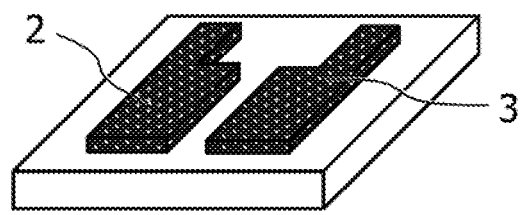
Figure 5C:
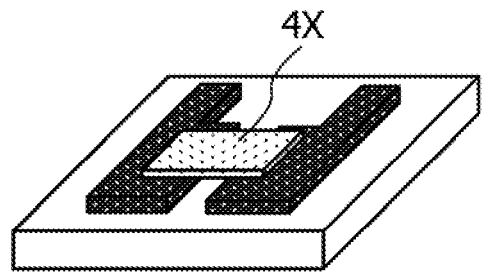

The shapes of the two electrodes 2 and 3 in FIG. 5B are an example and are not limiting as long as the shapes allow measurement of the resistance between the two electrodes 2 and 3. For example, the widths or gap width of the two electrodes 2 and 3 may be appropriately adjusted in consideration of the point of attachment of the sensor device, ease of the attachment, or the like. As illustrated as FIG. 5C, Cu (copper) is deposited so as to extend over the two gold electrodes (a pair of gold electrodes) 2 and 3 to form the Cu film 4X (Cu thin film; thickness of about 100 nm to about 120 nm). This step is a step of forming the Cu film 4X so as to connect the first electrode 2 and the second electrode 3 to each other.

Figure 5D:
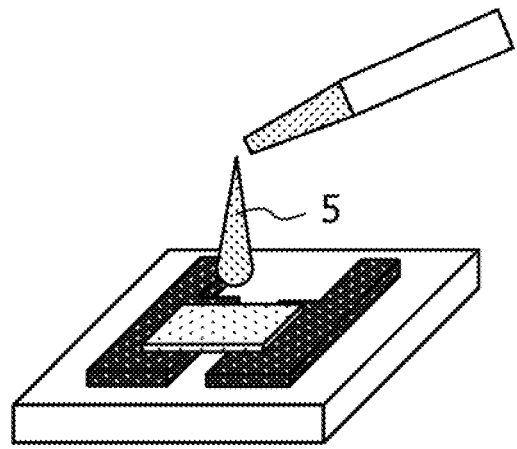

As illustrated as FIG. 5D, for example, about 100 μL of a PEDOT/PSS aqueous dispersion is dropped to about 10 mL of a methanol solution of about 0.02 M/L of cupric bromide ($CuBr_2$), and stirred. The resultant treatment liquid 5 is dropped onto the Cu film 4X deposited as described above; after a lapse of about 90 sec, the Cu film 4X is washed by rinsing with methanol, and dried. The treatment liquid 5 is a solution obtained by adding PEDOT/PSS to the $CuBr_2$ solution.

Figure 5E:
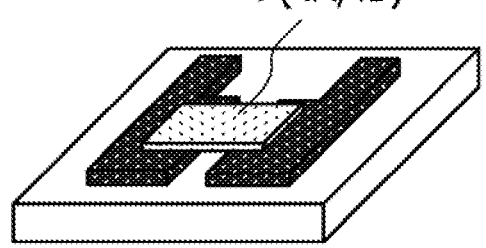

As a result, the Cu film 4X is changed, via the reaction of $Cu+CuBr_2 \rightarrow 2CuBr$, into the CuBr film 4A, so that, as illustrated as FIG. 5E, the PEDOT/PSS 4B bonds to the surfaces of crystal grains constituting the CuBr film 4A and the crystal grain boundaries, to form the sensitive film 4 extending over the two gold electrodes 2 and 3. This step is a step of forming the sensitive film 4, by treating the Cu film 4X with a treatment liquid containing Cu and the halogen element and prepared by adding PEDOT/PSS, the sensitive film 4 including the base film 4A containing Cu and the halogen element, and the PEDOT/PSS 4B bonding to the base film 4A.

In this case, the CuBr film 4A swells about 5 times as large as the original Cu film 4X, and the film thickness after the treatment is about 500 to about 800 nm. Examples of the solvent usable for cupric bromide include, in addition to methanol, water, ethanol, and 2-propanol. The treatment liquid 5 is dropped onto the Cu film 4X on the substrate 1, and the Cu film 4X is washed with methanol after a lapse of about 90 sec, and dried. However, this is not limiting. For example, the substrate 1 having the Cu film 4X deposited as described above may be immersed in the treatment liquid 5 (about 90 sec), and the substrate 1 may be washed with methanol, and dried.

In this way, the sensor device may be produced. The sensor device produced in this way measures the resistance (electrical resistance) between the two electrodes 2 and 3, to thereby sense gas near the sensor device, so that aldehyde is detected with high sensitivity. To the sensor device produced as described above, an arithmetic control unit (for example, a processor, a CPU, or a controller) is connected to constitute a gas sensor. The arithmetic control unit measures the resistance (resistance value) between the two electrodes of the sensor device (this function is referred to as a measurement unit), and converts a variation in the resistance value into concentration (in other words, for example, the ratio of the value of the variation in the resistance value is correlated with the concentration of aldehyde) (this function is referred to as a calculation unit), to thereby detect aldehyde near the sensor device with high sensitivity (for example, refer to FIG. 10 to FIG. 13).

In this case, the gas sensor (aldehyde gas sensor) includes the sensor device (aldehyde gas sensor device) constituted as described above, and an arithmetic control unit connected to the sensor device (for example, refer to FIG. 10 to FIG. 13). Thus, the sensor device, the method for producing the sensor device, and the gas sensor according to the embodiment provide advantages of enabling a sensor device for detecting aldehyde with high sensitivity and a gas sensor including the sensor device.

For example, aldehyde contained in gases such as breath gas or odors such as those of foods or old person smell is detected in rapid response with high sensitivity. For example, the above-described use of the PEDOT/PSS 4B for the sensitive film 4 has been found to cause an increased resistance value that is about 1000 to about 10000 times higher than the resistance value of a sensor (for example, an ammonia sensor) in which a CuBr film alone is used for the sensitive film.

The gas sensor measures the resistance (resistance value) between the two electrodes 2 and 3 of the sensor device, and converts the resistance to thereby determine the gas concentration. Thus, the resistance of the sensor (the resistance between the two electrodes of the sensor device; the resistance of the sensitive film) is preferably decreased in accordance with the circuit for measuring the resistance. In this case, PEDOT/PSS/PTS, which is prepared by further adding p-toluene sulfonic acid (PTS) to the PEDOT/PSS 4B, is preferably used for the sensitive film 4. The sensitive film 4 preferably further contains PTS. This is referred to as a first modification.

In this case, in the above-described production method according to the embodiment, a new treatment liquid is prepared by adding PTS to the above-described treatment liquid 5, and, as in the above-described case, the treatment liquid 5 may be dropped onto the substrate 1 having the Cu thin film 4X deposited, or the substrate 1 having the Cu thin film 4X deposited may be immersed in the treatment liquid 5. This enables a decrease in the resistance of the sensor. For example, a decrease in the resistance is achieved to a resistance about 1 to about 10 times higher than the resistance of a sensor (for example, an ammonia sensor) in which a CuBr film alone is used for the sensitive film. As a result, higher responsiveness is achieved, and higher sensitivity is achieved.

Figure 6:
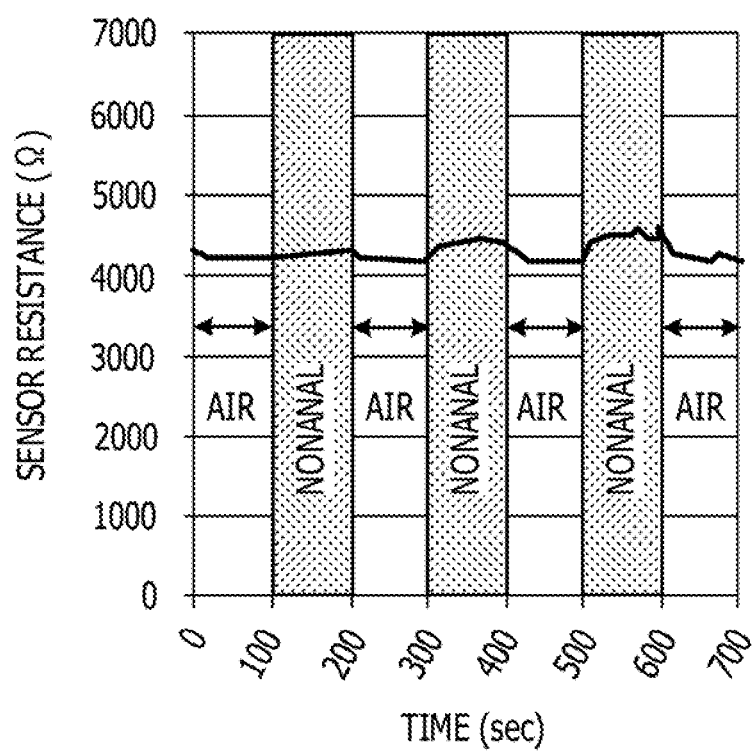
FIG. 6 illustrates an example of responses (to nonanal) of a gas sensor including a sensor device.

FIG. 6 illustrates a result obtained by exposing a sensor in which PEDOT/PSS/PTS is used for the sensitive film 4 to one of aldehyde gases, nonanal gas (about 300 ppb). Purging for a period of about 100 sec, and exposure to nonanal gas for about 100 sec were alternately performed three times. When the initial resistance value of the sensor is denoted by R0, and the resistance value of the exposed sensor is denoted by Rs, the response magnitude (sensitivity) of the sensor is represented by (Rs−R0)/R0×100(%).

With this formula, the sensor is found to have a response magnitude of about 12%, and has been confirmed to have performance sufficient for application to breath sensing. From introduction of nonanal gas switched from the background gas, the sensor resistance value reached the saturated region in about 20 to about 30 sec, which is a very fast response. From stopping of the introduction of nonanal gas and switching to the background gas, the sensor resistance value recovers in about 30 sec to a resistance value substantially the same as the sensor resistance value prior to the introduction.

Thus, it has been confirmed that a sensor having a large response magnitude, a short response time, and a fast recovery rate is provided. The repeatability was also good.

Figure 7:
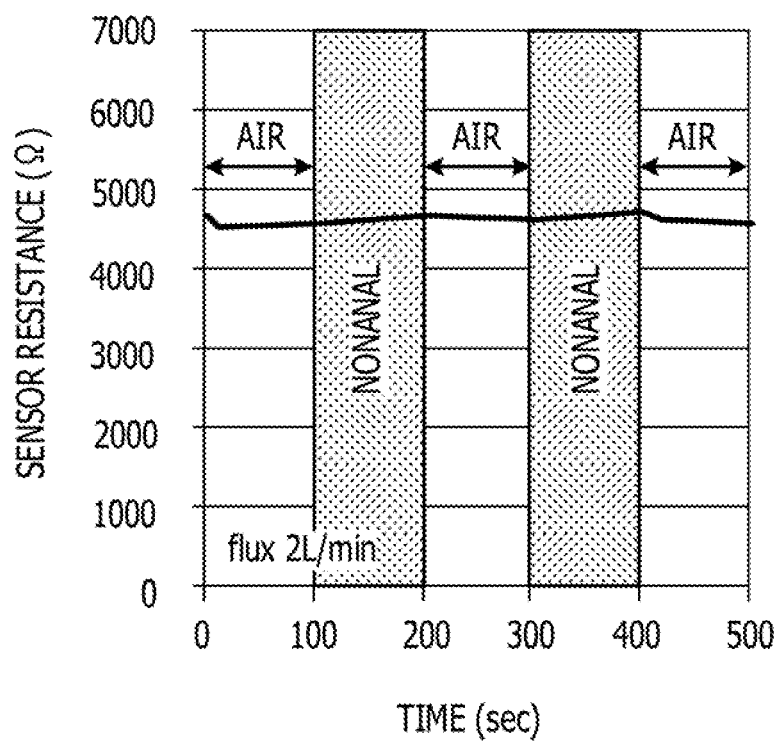
FIG. 7 illustrates an example of responses (to nonanal) of a gas sensor including a sensor device using a CuBr film alone as a sensitive film.

In order to confirm that PEDOT/PSS/PTS functions to detect nonanal gas, a sensor employing a CuBr film alone for the sensitive film was similarly exposed to nonanal gas; as a result, as illustrated as FIG. 7, this sensor was found to scarcely respond to nonanal gas.

This has confirmed that the sensor employing PEDOT/PSS/PTS for the sensitive film 4 functions to detect nonanal gas. The sensor employing the CuBr film alone for the sensitive film has an initial resistance of about 4.5 KΩ; it has been confirmed that substantially the same initial resistance is also achieved in the above-described sensor employing PEDOT/PSS/PTS for the sensitive film 4.

In the embodiment, nonanal gas is used to confirm the response; however, gases having an aldehyde group (aldehyde gases) are detectable. Examples of the gases having an aldehyde group include acetaldehyde, propionaldehyde, butanal, pentanal, hexanal, heptanal, and octanal. Thus, the gas sensor according to the embodiment is usable not only as a nonanal sensor for detecting nonanal, but also as an aldehyde sensor for detecting aldehydes.

The gas selectivity of the aldehyde sensor, namely, the response magnitude for each gas species was determined. As a result, for example, when the response magnitude for acetaldehyde gas is defined as 100, the response magnitude for nonenal gas was about 24.5, the response magnitude for ammonia gas was about 8.78, the response magnitude for ethanol gas was about 0.0459, and the response magnitude for acetone gas was about 1.43.

For example, the response magnitude for ammonia gas is about 1/10 of the response magnitude for acetaldehyde gas; when a detection target gas is a gas mixture of acetaldehyde gas and ammonia gas, use of the above-described aldehyde sensor alone does not provide the accurate concentration. However, a gas sensor employing a CuBr film alone for the sensitive film markedly responds to ammonia gas, but scarcely responds to other gas species; thus, sensing with a combination of this gas sensor and the above-described aldehyde sensor enables determination of the concentrations of ammonia and aldehyde.

For example, the above-described sensor employing PEDOT/PSS/PTS for the sensitive film 4 (first modification) has a response magnitude of about 12%, which is performance sufficient for application to breath sensing. However, as described above, actual breath contains a large number of gas species; in order to provide a sufficient response in actual breath, a larger response is desirably obtained.

Thus, in order to obtain a larger response, to the above-described sensitive film 4 employing PEDOT/PSS/PTS, nonanal ($C_8H_{17}CHO$) serving as the detection target is preferably further added, to provide a sensor employing PEDOT/PSS/PFTS+nonanal for the sensitive film 4. This is referred to as a second modification. In this case, in the above-described production method according to the embodiment, a new treatment liquid may be prepared by adding a nonanal solution (here, dropping about 50 µL of nonanal) to the above-described treatment liquid 5; and, as in the above-described case, the treatment liquid 5 may be dropped onto the substrate 1 having the Cu thin film 4X deposited, or the substrate 1 having the Cu thin film 4X deposited may be immersed in the treatment liquid 5.

Figure 8:
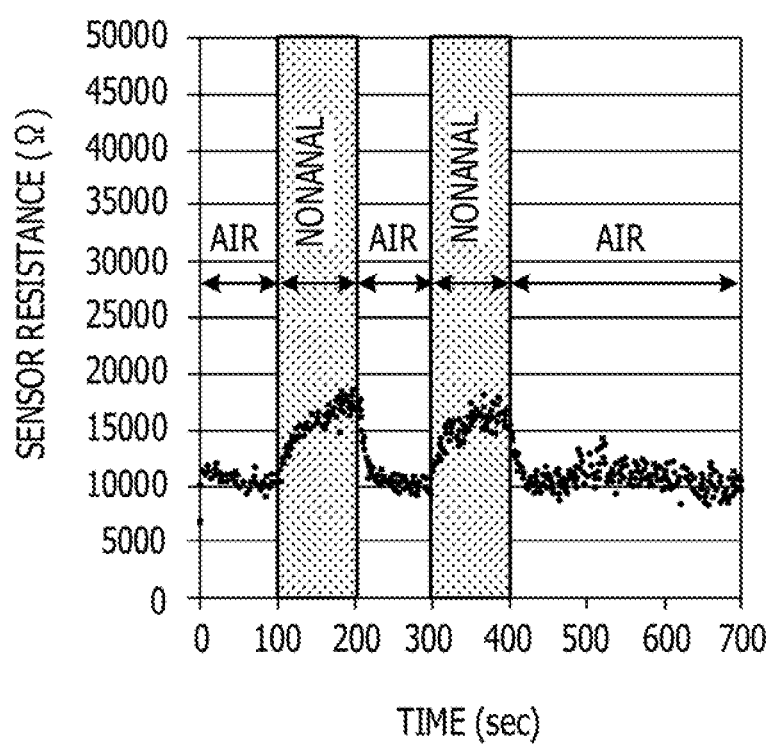
FIG. 8 illustrates an example of responses (to nonanal) of a gas sensor including a sensor device.

Nonanoic acid, which is a carboxylic acid obtained by oxidization of nonanal, may be added, to provide similar advantages. In this case, a new treatment liquid may be used that is prepared by dropping (adding) nonanoic acid to the above-described treatment liquid 5. FIG. 8 illustrates a result obtained by exposing the sensor employing PEDOT/PSS/

PTS+nonanal for the sensitive film 4, to one of aldehyde gases, nonanal gas (about 300 ppb) as in the above-described first modification.

Figure 9:
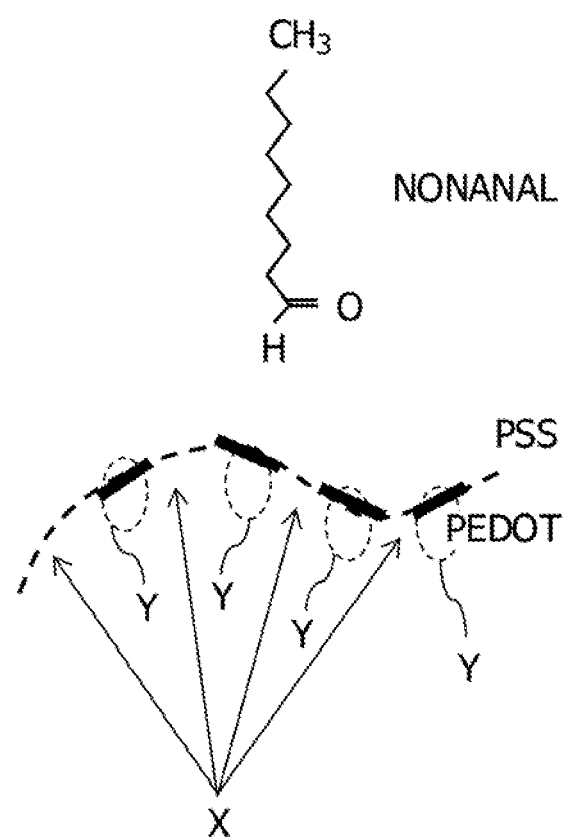
FIG. 9 illustrates an example of adsorption of nonanal onto a sensitive film of a gas sensor including a sensor device.

The sensor employing PEDOT/PSS/PTS+nonanal for the sensitive film 4 has an initial resistance about 3 times higher than that of a sensor employing a CuBr film alone for the sensitive film, but has a markedly increased sensitivity of about 180%. This is because, as illustrated as FIG. 9, the added nonanal adsorbs onto PEDOT-non-adsorption portions of PSS (portions denoted by symbol X in FIG. 9); thus, nonanal having entered as gas from the outside comes close to PEDOT-adsorption portions of PSS (portions denoted by symbol Y in FIG. 9) that directly affect electroconductivity, and strongly acts on PSS, to strongly attract the positive charges of PSS to the aldehyde group.

As a result, the aldehyde group is electrically oxidized. Since the PEDOT-adsorption portions of PSS serve as electroconductive paths, there is inferentially a mechanism in which a decrease in the number of adsorption portions due to the aldehyde group causes a decrease in the electroconductivity and an increase in the resistance. The case of further adding nonanal to the above-described sensitive film 4 employing PEDOT/PSS/PTS according to the first modification is described as an example; however, this is not limiting. For example, nonanal may be further added to the above-described sensitive film 4 employing PEDOT/PSS according to the embodiment to provide a sensor employing PEDOT/PSS+nonanal for the sensitive film 4.

Since the detection target is nonanal, nonanal or nonanoic acid is added to the sensitive film 4. However, this is not limiting as long as, for example, the detection target is an aldehyde; in this case, an aldehyde or carboxylic acid may be added to the sensitive film 4. In this case, compared with the above-described embodiment and first modification, the sensitive film 4 further contains the aldehyde or carboxylic acid. For example, as described later, when the detection target is nonenal, nonenal may be added to the sensitive film 4. In this case, compared with the above-described embodiment and first modification, the sensitive film 4 further contains nonenal as an aldehyde.

In this case, the substance dropped (added) to the above-described treatment liquid 5 may be a substance containing an aldehyde group or a substance containing a carboxylic add that is obtained by oxidization of the above-described substance. For example, as described above, when the detection target is nonanal, the substance containing an aldehyde group may be an organic compound having one or more —CHO groups and having R in which the straight chain has 1 to 9 carbon atoms. For example, as described later, when the detection target is nonenal, the substance containing an aldehyde group may be an organic compound having one or more —CHO groups, and having R having one or more unsaturated bonds and 1 to 9 carbon atoms.

The above-described amount of dropping (addition) to the treatment liquid 5 is not limited to about 50 µL, and larger amounts and smaller amounts provide the effect; however, the amount is preferably appropriately adjusted in accordance with the substance dropped and the treatment conditions so as to provide a greater effect. For example, the above-described embodiment and modifications are described with, as examples, cases of application to aldehyde sensors (for example, nonanal sensors) for detecting an aldehyde (for example, nonanal); however, this is not limiting. The sensor devices and gas sensors including these according to the above-described embodiment and modifications are also applicable to ketone sensors (for example, acetone sensors) for detecting a ketone (for example, acetone).

Aldehyde and ketone share a structural feature of having a carbonyl group. The C atom of the carbonyl group is positively polarized, and this portion considerably contributes to gas reactivity. Thus, a gas sensor responding to aldehyde gas is also applicable to ketone gas from the viewpoint of the mechanism; the gas sensor also exhibits responsiveness for ketone gas, the responsiveness being similar to the responsiveness for aldehyde gas, though the response magnitude is different.

Since alkyl groups function as electron-donating groups to reduce polarization, compared with aldehyde having a single alkyl group, ketone having two alkyl groups has a low degree of polarization. Thus, the reaction of ketone is relatively weak. Thus, the sensor devices and gas sensors including these according to the above-described embodiment and modifications are also applicable to ketone sensors (for example, acetone sensors) for detecting a ketone (for example, acetone).

When the above-described second modification is applied to a ketone sensor, the detection target is a ketone (for example, acetone), so that a ketone (for example, acetone) may be added to the sensitive film 4. In this case, compared with the above-described embodiment and the first modification, the sensitive film 4 further contains a ketone (for example, acetone).

A case will be described with reference to FIG. 10 in which a sensor device and a gas sensor including this according to the above-described embodiment or modifications are used as a breath gas sensor, and applied to a breath gas sensor system. This is referred to as a first application example. As illustrated as FIG. 10, a breath gas sensor system (information processing system) 10 will be described as an example, the breath gas sensor system 10 including a breath gas sensor (gas sensor) 8 including two sensor devices that are a sensor device (aldehyde sensor device) 6 according to the above-described embodiment or modifications, and a sensor device (ammonia sensor device) 7 employing a CuBr film alone as a sensitive film, and a computer 9 [for example, a personal computer (PC) or a portable terminal such as a smartphone] for processing data obtained with the breath gas sensor 8.

Figure 10:
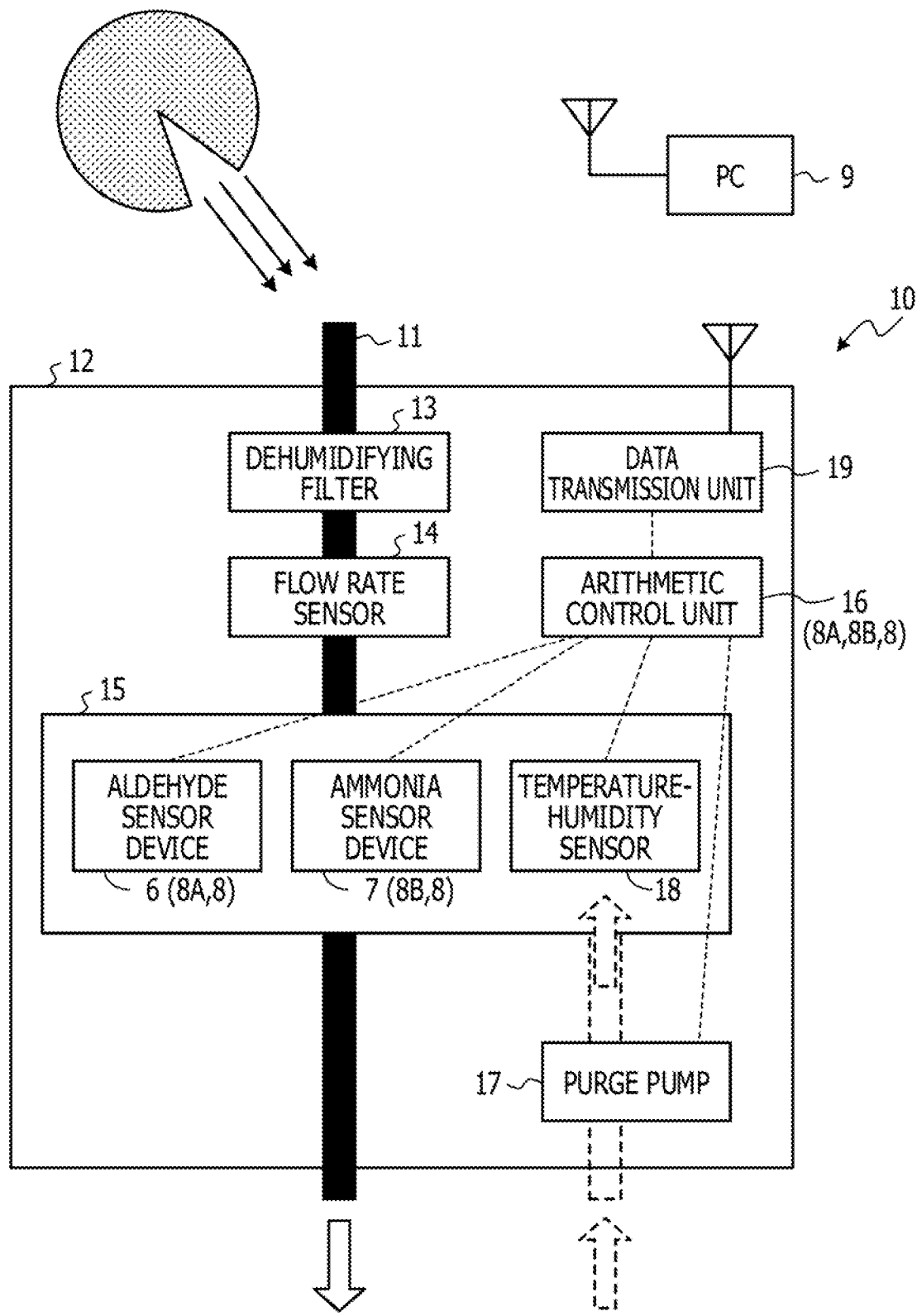
FIG. 10 illustrates an example of the case of application of a sensor device and a gas sensor to a breath gas sensor system.

In this breath gas sensor system 10, as illustrated as FIG. 10, breath is introduced through a breath inlet 11 into a chamber 12, and is introduced through a dehumidifying filter 13 and a flow rate sensor 14 into a sensor chamber 15. The breath blown into the inlet 11 is changed with the dehumidifying filter 13 from a high humidity of about 80% RH or more to a low humidity of about 30% RH.

The flow rate sensor 14 is used and the breath may be adjusted so as to be blown into at a constant flow rate. For example, a method may be considered in which the flow rate is indicated with a level meter, and a subject adjusts the blowing strength such that the level becomes constant. For example, a mechanism may be disposed in which, upon detection of reaching a certain flow rate or more with the flow rate sensor 14, a solenoid valve performs switching between channels to introduce breath into the chamber 15.

The sensor chamber 15 includes the aldehyde sensor device 6 and the ammonia sensor device 7 serving as breath sensor devices, and these are connected to an arithmetic control unit 16.

The arithmetic control unit 16 is configured to convert responses (here, variations in resistance values) of the aldehyde sensor device 6 and the ammonia sensor device 7 into concentrations, to thereby determine the concentrations of aldehyde and ammonia.

The aldehyde sensor device 6 and the arithmetic control unit 16 constitute an aldehyde sensor 8A. The ammonia sensor device 7 and the arithmetic control unit 16 constitute an ammonia sensor 8B. In summary, the breath gas sensor 8 includes the aldehyde sensor 8A for detecting aldehyde in breath gas, and the ammonia sensor 8B for detecting ammonia in breath gas.

The ammonia sensor BB selectively detects ammonia. Thus, these two sensors 8A and 8B are simultaneously used to thereby determine the concentrations of aldehyde gas and ammonia gas. As described above, the aldehyde sensor 8A also exhibits some sensitivity to ammonia. Thus, in the case of breath gas simultaneously containing ammonia gas and aldehyde gas, it is difficult to accurately determine the concentration of aldehyde gas.

However, the ammonia sensor 8B selectively detects ammonia gas. Thus, these two sensors 8A and 8B are simultaneously used to thereby determine the concentrations of aldehyde gas and ammonia gas. For example, the response of the ammonia sensor 8B may be used to determine the concentration of ammonia gas; a value corresponding to this concentration of ammonia gas may be subtracted from a value corresponding to the response of the aldehyde sensor 8A, to determine the concentration of aldehyde gas.

To the sensor chamber 15, a purge pump 17 is connected. For every measurement, the sensor chamber 15 is purged with the purge pump 17. Within the sensor chamber 15, a temperature-humidity sensor 18 is disposed and used for the purpose of correcting responses of the gas sensors 8A and 8B in accordance with temperature or humidity, or monitoring the progress of purging. The arithmetic control unit 16 is configured to use a data transmission unit 19 to transmit such data (concentration data), for example, wirelessly to an outer computer 9 (for example, a PC or a portable terminal).

The data obtained with the breath gas sensor 8 is processed with the computer 9 to display, on the screen of the computer 9, for example, an indicator of the concentration of the target gas component (here, aldehyde and ammonia), or whether or not being suffered from disease. On the chamber 12 of the breath gas sensor 8, an indicator unit may be disposed to indicate, for example, an indicator of the concentration of the target gas component (here, aldehyde and ammonia).

The computer 9 for processing data obtained with the breath gas sensor 8 is described as, for example, a PC or a portable terminal. However, this is not limiting, and the computer 9 may be a server such as a cloud server. For example, data obtained with the breath gas sensor 8 (or, for example, data having been processed with a PC or a portable terminal) may be transmitted to a server (for example, a cloud server) connected via a network to a PC or a portable terminal, to process the data with the server.

In this case, data measured with the breath gas sensor 8 may be collected via the network, and accumulated to construct a database; such data may be analyzed, and the results may be fed back. This is effectively used for, for example, enhancement of the accuracy of screening of a disease, and studies as to whether or not the disease correlates with another disease; and the measurement results may be fed back without laborious work. For example, analysis is performed as to whether or not a subject of breath measurement has cancer, or as to correlation with another disease; this enables enhancement of the accuracy of screening or expansion to screening of another disease.

The breath gas sensor 8 including two sensors that are the aldehyde sensor 8A and the ammonia sensor 8B is described as an example. However, this is not limiting. A breath gas sensor may be constituted so as to include one or more gas sensors that respond to a gas component in breath.

Hereinafter, a case will be described with reference to FIG. 11 and FIG. 12 in which a sensor device and a gas sensor including this according to the above-described embodiment or modifications are used as an odor sensor (odor gas sensor) and applied to a food freshness determination system. This is referred to as a second application example.

The sensor devices (aldehyde sensor devices) according to the above-described embodiment and modifications may be used not only for, as in the first application example, detecting aldehyde contained in breath gas, but also for, as in this second application example, sensing the freshness of food. As illustrated as FIG. 11 and FIG. 12, a food freshness determination system (information processing system) 23 will be described as an example, the food freshness determination system 23 including an odor sensor (gas sensor) 21 including a sensor device (aldehyde sensor device) 20 according to the above-described embodiment or modifications, and a computer 22 [for example, a personal computer (PC) or a portable terminal such as a smartphone] for processing data obtained with the odor sensor 21.

Aldehyde gas is known to generate in decomposition of, for example, high-lipid-content foods such as dairy products. This is because, in the foods, polyunsaturated fatty acids constituting lipids are oxidized into, via hydroperoxide intermediates, aldehydes.

Concerns are rising that food becomes less safe and less reliable. However, the odor sensor (aldehyde gas sensor) 21 including the sensor device (aldehyde sensor device) 20 according to the above-described embodiment or modifications may be used to monitor the odor of food, to thereby, for example, quantitatively measure the degree of decomposition of food immediately before consumption.

Figure 11:
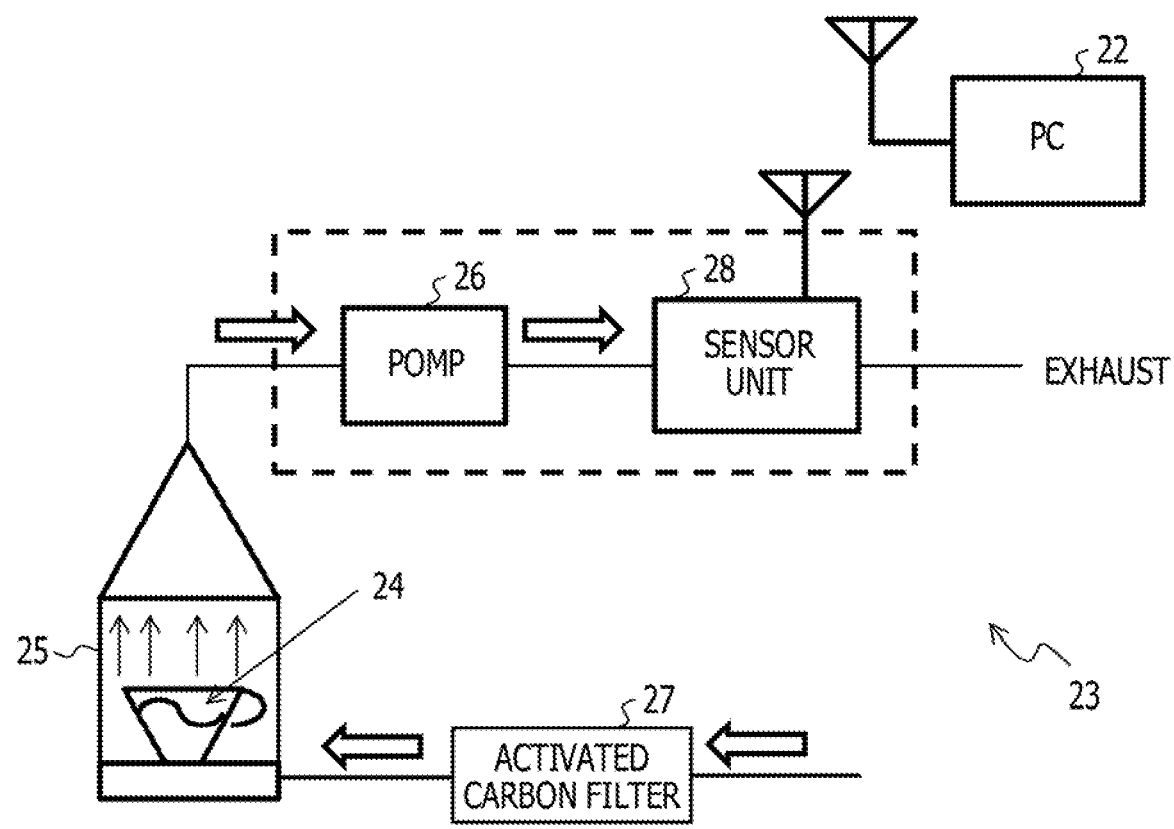
FIG. 11 illustrates an example of the case of application of a sensor device and a gas sensor to a food freshness determination system.

As illustrated as FIG. 11, in this food freshness determination system, a pump 26 is connected to the suction port of a food chamber 25 into which a food serving as a test target (freshness determination target) 24 is placed; the outside air having passed through a filter (here, an active carbon filter) 27 and gas (odor) generated from the food 24 are suctioned, and introduced into a sensor unit 28. As illustrated as FIG. 12, the sensor unit 28 includes a sensor chamber 29, the sensor chamber 29 including the aldehyde sensor device (sensor device) 20 serving as an odor sensor device, which is connected to an arithmetic control unit 30; and includes a data transmission unit 31.

The arithmetic control unit 30 is configured to convert the response (here, a variation in the resistance value) of the aldehyde sensor device 20 into concentration, to determine the concentration of aldehyde. In this case, the aldehyde sensor device 20 and the arithmetic control unit 30 constitute the aldehyde sensor 21, which is used as an odor sensor (gas sensor) for detecting aldehyde contained in the odor of the food 24.

As illustrated as FIG. 11, the food 24 is placed into the food chamber 25 serving as an odor sampling chamber; while the outside air is taken through the active carbon filter 27 into the chamber 25, the odor of the food 24 is suctioned with the pump 26. The suctioned odor is passed through the aldehyde sensor device 20 (refer to FIG. 12) for detecting aldehyde contained in the odor of the food 24, and exhausted.

Figure 12:
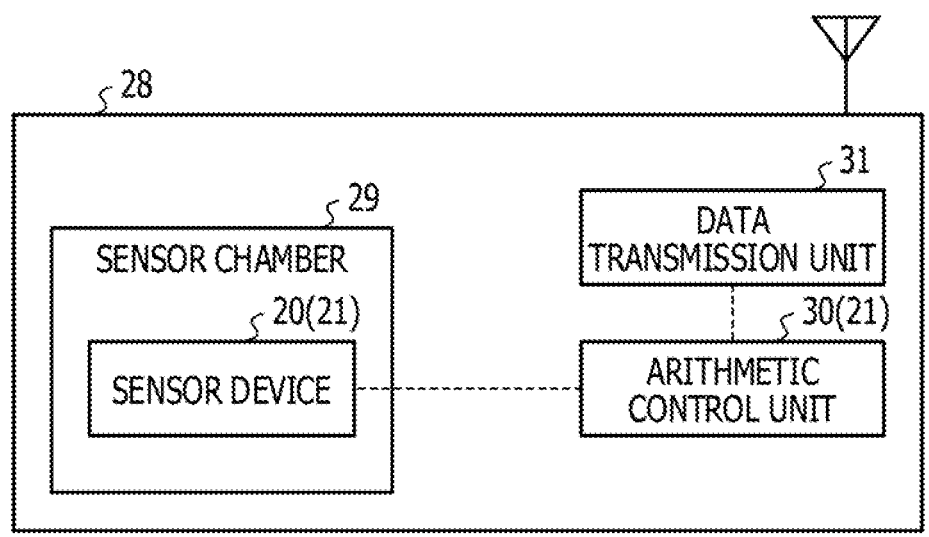
FIG. 12 illustrates an example of a sensor unit in the case of application of a sensor device and a gas sensor to a food freshness determination system.

The response (here, the resistance value) of the aldehyde sensor device varies in accordance with the concentration of aldehyde contained in the odor; thus, the arithmetic control unit 30 is configured to convert such a variation into the concentration of aldehyde, to thereby determine the concentration of aldehyde contained in the odor of the food (refer to FIG. 12). The arithmetic control unit 30 is configured to transmit this data (concentration data) by using the data transmission unit 31 (refer to FIG. 12), for example, a wireless system such as Bluetooth (registered trademark) to an outside computer 22 (for example, a PC or a portable terminal) (refer to FIG. 11).

The data obtained with the odor sensor 21 (refer to FIG. 12) is processed with the computer 22 (for example, a PC or a portable terminal) to determine the freshness of the food in accordance with the concentration of aldehyde; and information, for example, an indicator of the concentration of aldehyde or the degree of freshness of the food is displayed on the screen. The arithmetic control unit 30 (refer to FIG. 12) of the odor sensor 21 may be configured to determine the freshness of the food in accordance with the concentration of aldehyde; a display unit may be disposed on the chamber of the sensor unit 28, and used to display information, for example, the indicator of the concentration of aldehyde or the degree of freshness of the food.

For example, though the indicator of decomposition varies in accordance with the reference gas, a food that, for example, has just been purchased and definitely has high freshness may be sensed to provide a reference, and the freshness of a target food may be determined, to thereby determine the degree of decomposition more accurately. The computer 22 (refer to FIG. 11) for processing the data obtained with the odor sensor 21 (refer to FIG. 12) is described as, for example, a PC or a portable terminal. However, this is not limiting. For example, a server such as a cloud server may be used. For example, the data obtained with the odor sensor 21 (or, for example, data having been processed with a PC or a portable terminal) may be transmitted to a server (for example, a cloud server) connected via a network to a PC or a portable terminal, to process the data with the server.

Hereinafter, a case will be described with reference to FIG. 13 in which a sensor device and a gas sensor including this according to the above-described embodiment or modifications are used as an odor sensor (odor gas sensor), and applied to an odor checker. This is referred to as a third application example. For example, the sensor devices (aldehyde sensor devices) according to the above-described embodiment and modifications have been found to respond to also nonenal contained in odor.

Nonenal is a gas component well-known as the main component of old person smell. Thus, as illustrated as FIG. 13, a sensor device 32 (aldehyde sensor device; nonenal sensor device) according to the above-described embodiment or modifications may be used as an old person smell sensor 33 (nonenal sensor; odor sensor) for detecting nonenal contained in odor, and applied to an old person smell checker 34 (nonenal gas checker; odor checker).

Figure 13:
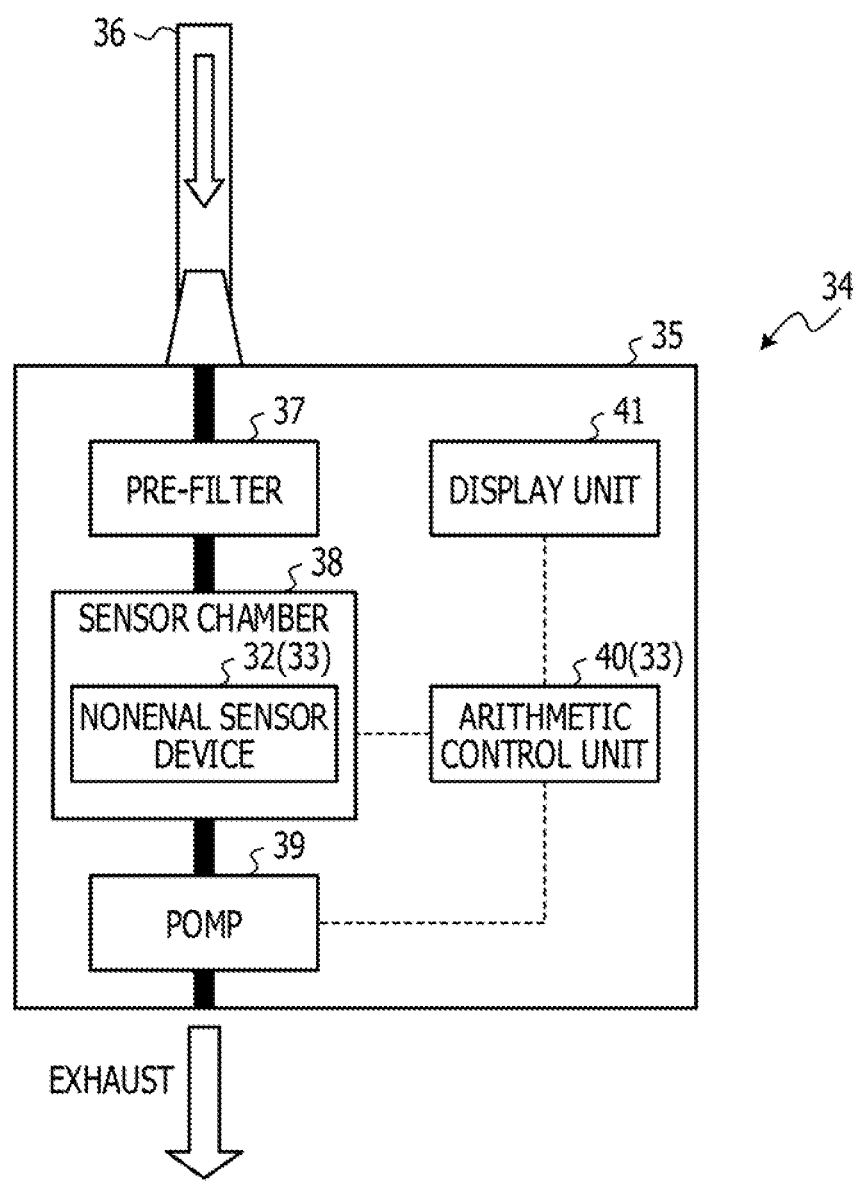
FIG. 13 illustrates an example of the case of application of a sensor device and a gas sensor to an odor checker (nonenal gas checker)

In this old person smell checker 34, for example, as illustrated as FIG. 13, the outside air is introduced from an inlet 36 disposed on a chamber 35, through a pre-fitter 37, into a sensor chamber 38. A pump 39 is contained. This pump 39 is configured to suction the outside air so as to be introduced from the inlet 36 into the sensor chamber 38, and exhausted.

Within the sensor chamber 38, the nonenal sensor device 32 is disposed as an odor sensor device, and this is connected to an arithmetic control unit 40. The arithmetic control unit 40 is configured to convert a response of the nonenal sensor device 32 (here, a variation in the resistance value) into concentration, to determine the concentration of nonenal, and display the result on an indication unit 41 (indicator).

In this case, the nonenal sensor device 32 and the arithmetic control unit 40 constitute the nonenal sensor 33, which is used as an old person smell sensor for detecting nonenal contained in odor. The case is described as an example in which the sensor device 32 according to the above-described embodiment or modifications is used as the old person smell sensor 33 for detecting nonenal contained in odor, and applied to the old person smell checker 34. However, this is not limiting. For example, the sensor devices according to the above-described embodiment and modifications may each be used as an odor sensor for detecting aldehyde contained in odor, and applied to an odor checker.

As in the first application example and second application example, a data transmission unit (communication unit) may be disposed to transmit data to, for example, a PC, a portable terminal, or a computer such as a server, and the computer may process the data. The case is described as an example in which a single sensor device 32 according to the above-described embodiment or modifications is used; however, this is not limiting, and a plurality of sensor devices 32 may be used.

There are various places and scenes to which an odor checker for sensing an odor such as old person smell is applicable, and the way of using the odor checker varies depending on the place or scene. For example, the odor checker may be disposed in a cabin of a train, a bus, or the like to monitor the indoor air environment, which may be used as an indicator for determining the amount of ventilation. A case will be described with reference to FIG. 14A, FIG. 14B, and FIG. 15 in which a sensor device and a gas sensor including this according to the above-described embodiment or modifications are used as a breath gas sensor or an odor sensor (odor gas sensor; old person smell sensor), and applied to, for example, a portable terminal such as a smartphone or a watch-type wearable terminal. This is referred to as a fourth application example.

Figure 14A:
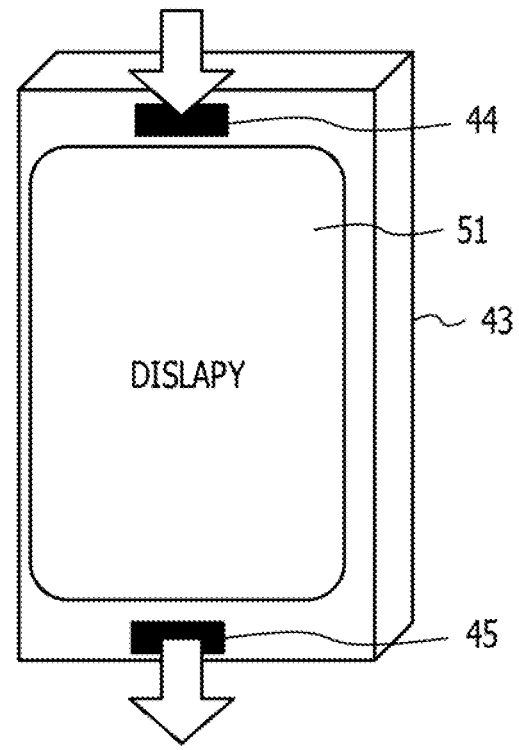
FIG. 14A and FIG. 14B illustrate an example of the case of application of a sensor device and a gas sensor to a smartphone.
Figure 14B:
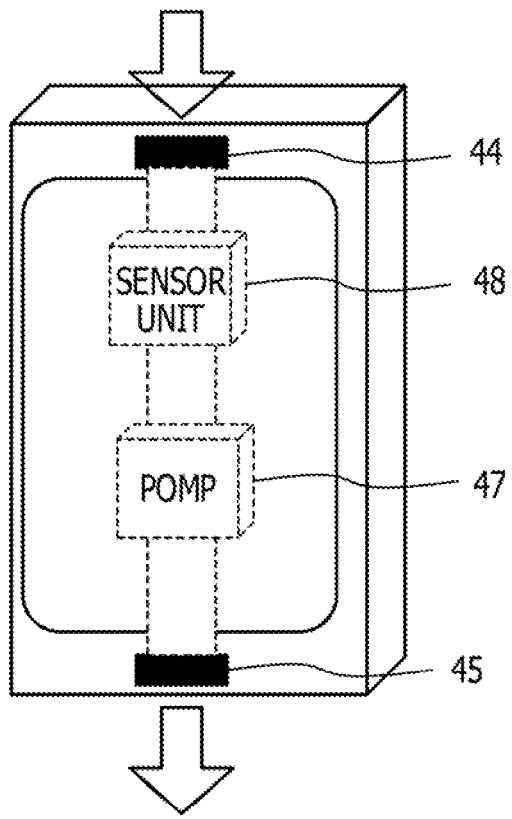

As illustrated as FIG. 14A, FIG. 14B, and FIG. 15, a case will be described as an example in which a sensor device 42 according to the above-described embodiment or modifications is mounted on a smartphone 43, and used for monitoring breath gas or odor. As illustrated as FIG. 14A and FIG. 14B, in this smartphone 43 containing the gas sensor, a hole 44 in a speaker unit and a microphone hole 45 in the smartphone 43 are also used as the target gas suction port and exhaust port of a breath gas sensor or odor gas sensor 46 contained in the smartphone 43.

The smartphone 43 contains an ultrasmall pump 47, and is configured to suction the outside air through the speaker hole 44, to introduce the outside air into a sensor unit 48, and exhaust the air through the microphone hole 45. The ultrasmall pump 47 is preferably, for example, a piezoelectric pump from the viewpoint of size and flow rate, or may be, for example, a diaphragm pump or a sirocco fan.

Figure 15:
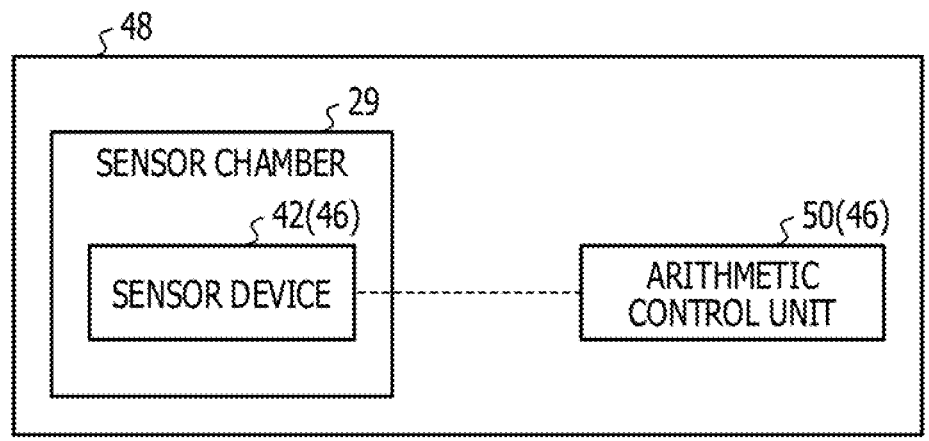
FIG. 15 illustrates an example of a sensor unit in the case of application of a sensor device and a gas sensor to a smartphone.

As illustrated as FIG. 15, the sensor unit 48 includes a sensor chamber 49. Within the sensor chamber 49, as the breath sensor device or odor sensor device 42, a sensor device according to the above-described embodiment or modifications is disposed, and is connected to an arithmetic control unit 50. The arithmetic control unit 50 is configured to convert a response of the sensor device 42 (here, a variation in the resistance value) into concentration, to determine the concentration of aldehyde (for example, nonanal or nonenal), and to display the result on a display 51 of the smartphone 43 [refer to FIG. 14A].

In this case, the sensor device 42 and the arithmetic control unit 50 constitute the gas sensor 46 (breath gas sensor or odor sensor). The arithmetic control unit 50 may be an arithmetic control unit of the smartphone 43, or an arithmetic control unit that is not the arithmetic control unit of the smartphone 43, but is disposed within the smartphone 43. When the arithmetic control unit 50 is the arithmetic control unit of the smartphone 43, the sensor device 42 mounted on the smartphone 43 and the arithmetic control unit of the smartphone 43 constitute the gas sensor 46.

When the gas sensor 46 including the sensor device 42 according to the above-described embodiment or modifications is used as, for example, an old person smell sensor, the gas sensor contained may be configured to operate during calls. For example, when the gas sensor 46 is used as a breath gas sensor, the introduction port may be provided on the microphone side, and the exhaust port may be provided on the speaker side, to provide a breath gas sensor.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A sensor device comprising:
a first electrode and a second electrode disposed over a substrate; and
a sensitive film including:
a base film which couples the first electrode and the second electrode to each other and contains Cu and a halogen element; and
PEDOT/PSS which bonds to the base film.

2. The sensor device according to claim 1, wherein the PEDOT/PSS bonds to grain boundaries of crystal grains which is included in the base film, and surfaces of the crystal grains.

3. The sensor device according to claim 1, wherein the sensitive film includes PTS.

4. The sensor device according to claim 1, wherein the sensitive film includes an aldehyde or carboxylic acid.

5. The sensor device according to claim 4, wherein the aldehyde is nonanal.

6. The sensor device according to claim 4, wherein the aldehyde is nonenal.

7. The sensor device according to claim 4, wherein the carboxylic acid is nonanoic acid.

8. The sensor device according to claim 1, wherein the sensitive film includes a ketone.

9. The sensor device according to claim 8, wherein the ketone is acetone.

10. A method for producing a sensor device, comprising:
forming a first electrode and a second electrode over a substrate;
forming a Cu film so as to couple the first electrode and the second electrode to each other; and
forming a sensitive film by treating the Cu film with a treatment liquid which contains Cu and a halogen element and is processed by adding PEDOT/PSS, the sensitive film including a base film containing Cu and the halogen element, and PEDOT/PSS which bonds to the base film.

11. The method according to claim 10, wherein a treatment liquid which is obtained by further adding PTS to the treatment liquid is used as the treatment liquid in the forming the sensitive film.

12. The method according to claim 10, wherein a treatment liquid which is obtained by further adding an aldehyde or carboxylic acid to the treatment liquid is used as the treatment liquid in the forming the sensitive film.

13. The method according to claim 12, wherein a treatment liquid which is obtained by adding nonanal to the treatment liquid is used as the treatment liquid in the forming the sensitive film.

14. The method according to claim 12, wherein the treatment liquid used in the forming of the sensitive film is a treatment liquid which is obtained by adding nonenal to the treatment liquid is used as the treatment liquid in the forming the sensitive film.

15. The method according to claim 12, wherein the treatment liquid used in the forming of the sensitive film is a treatment liquid which is obtained by adding nonanoic acid to the treatment liquid is used as the treatment liquid in the forming the sensitive film.

16. The method according to claim 10, wherein the treatment liquid used in the forming of the sensitive film is a treatment liquid which is obtained by further adding a ketone to the treatment liquid is used as the treatment liquid in the forming the sensitive film.

17. The method according to claim 16, wherein the treatment liquid used in the forming of the sensitive film is a treatment liquid which is obtained by adding acetone to the treatment liquid is used as the treatment liquid in the forming the sensitive film.

18. A gas sensor comprising:
a sensor device; and
a processor coupled to the sensor device,
the sensor device includes:
a first electrode and a second electrode disposed over a substrate; and
a sensitive film including:
a base film which couples the first electrode and the second electrode to each other and contains Cu and a halogen element; and
PEDOT/PSS which bonds to the base film.

19. The gas sensor according to claim 18, wherein the PEDOT/PSS bonds to grain boundaries of crystal grains which is included in the base film, and surfaces of the crystal grains.

20. The gas sensor according to claim 18, wherein the processor acquires a resistance value between the first electrode and the second electrode, and converts a variation in the resistance value into concentration related to the sensitive film.

* * * * *